United States Patent [19]

Motoki et al.

[11] Patent Number: 6,031,130
[45] Date of Patent: Feb. 29, 2000

[54] METHOD FOR PREPARING N,N-DISUBSTITUTED HYDROXYLAMINES

[75] Inventors: Masuji Motoki; Tadahisa Sato, both of Kanagawa, Japan

[73] Assignee: Fuji Photo Film Co., Ltd., Kanagawa, Japan

[21] Appl. No.: 09/081,943

[22] Filed: May 21, 1998

[30] Foreign Application Priority Data

May 29, 1997 [JP] Japan ..................... 9-139517

[51] Int. Cl.$^7$ ................ C07C 239/00; C07C 259/00
[52] U.S. Cl. ................ 562/800; 564/300; 564/301; 430/250
[58] Field of Search .................. 564/300, 301; 430/250; 562/800

[56] References Cited

U.S. PATENT DOCUMENTS

| | | | |
|---|---|---|---|
| 3,293,034 | 12/1966 | Green et al. .......................... | 430/250 |
| 3,491,151 | 1/1970 | Bader .................................. | 564/301 |
| 4,782,105 | 11/1988 | Ravichandran et al. ............ | 524/236 |

OTHER PUBLICATIONS

Synthesis of Nitrones by Methyltrioxorhenium Catalyzed Direct Oxidation of Secondary Amines; *Tetrahedron Letters*, vol. 37, No. 33, pp. 6025–6028, 1996.

*Primary Examiner*—Gary L. Kunz
*Assistant Examiner*—Everett White
*Attorney, Agent, or Firm*—Sughrue, Mion, Zinn, Macpeak & Seas, PLLC

[57] ABSTRACT

A method for preparing N,N-disubstituted hydroxylamine compounds represented by the formula (II): HO—N($R^1$)($R^2$) wherein $R^1$ and $R^2$ may be the same or different, and independently represent a substituted or unsubstituted alkyl group, a substituted or unsubstituted aryl group, or a substituted or unsubstituted aromatic heterocyclic group, which comprises the step of adding a rhenium catalyst and aqueous hydrogen peroxide to a mixture containing a secondary amine compound represented by the formula (I): HN($R^1$)($R^2$) wherein $R^1$ and $R^2$ have the same meanings as those defined above and a dehydrating agent.

19 Claims, No Drawings

METHOD FOR PREPARING N,N-DISUBSTITUTED HYDROXYLAMINES

BACKGROUND OF THE INVENTION

1. Field of the Invention

The present invention relates to a novel method for preparing N,N-disubstituted hydroxylamine compounds which are useful as developing agents of silver halide photosensitive materials and additives for polymers.

2. Related Art

N,N-Dialkylhydroxylamine compounds are know to have suitable capabilities for developing agents of silver halide photosensitive materials as described in Japanese Patent Publication (KOKOKU) No. (Sho) 42-2794/1967. On the basis of the excellent capabilities, they have been widely and practically used as diffusion transfer-type developers in recent years. N,N-Dialkylhydroxylamine compounds are also useful as process stabilizers for polyolefin compositions in the presence of auxiliary stabilizing agents such as phenolic antioxidants (U.S. Pat. No. 4,590,231), and useful as stabilizer for arylene sulfide resins utilizing antioxidants based on phenolic amides or esters (U.S. Pat. No. 4,464,122).

Several methods for preparing N,N-dialkylhydroxylamine compounds have been known so far. U.S. Pat. No. 3,293,034 and Japanese Patent Publication (KOKAI) No. (Sho) 42-2794/1967 disclose methods for preparing N,N-dialkylhydroxylamine compounds which comprises the step of oxidizing dialkylamine compounds by using hydrogen peroxide. However, these methods are not preferred because they can achieve only a poor yield and the reactions entail a temperature of 50 to 60° C., which involves risk of explosion.

U.S. Pat. No. 3,655,764 discloses a method for preparing N,N-dialkylhydroxylamine compounds by oxidizing dialkylamine compounds using hydrogen peroxide, which includes the addition of a chelating agent such as ethylenediaminetetraacetic acid (EDTA). U.S. Pat. No. 3,661,996 discloses a method for purifying a resulting N,N-dialkylhydroxylamine compound by means of a special apparatus which utilizes a strongly acidic ion exchange resin. However, both methods have several problems, e.g., they only give an insufficient yield of approximately 50%, and the latter method requires the special apparatus.

U.S. Pat. No. 3,491,151 discloses a method for preparing N,N-dialkylhydroxylamine compounds by allowing hydroxylamines react with alkyl halides, alkyl tosylates or the like. However, this method is also undesirable, because it requires a prolonged reaction time and achieves a yield of no more than about 50%. Tetrahedron Letters, Vol. 37, No. 33 pp. 6025–6028, 1996 discloses a method for synthesizing nitrone compounds by oxidizing dibenzylamine by means of a combination of aqueous hydrogen peroxide and methyltrioxorhenium. According to this synthetic method, an N,N-dibenzylhydroxyl-amine compound is produced in addition to a nitrone compound as a major product. However, its yield is low. Furthermore, the method requires a large amount of methyltrioxorhenium. For these reasons, the method is only disadvantageously applied to practical preparations of N,N-dibenzylhydroxylamine compounds.

Japanese Patent No. 2,567,656 discloses a method comprising the steps of first synthesizing a tertiary amine compound, and then treating the resulting tertiary amine compound with aqueous hydrogen peroxide to form an N-oxide compound, followed by producing an N,N-dialkylhydroxylamine compound according to the reverse Michael reaction. However, this method involves a lot of reaction steps because it needs the preparation of the tertiary amine compound. The method is also disadvantageous from a viewpoint of safety, because it requires a high concentration of aqueous hydrogen peroxide. Further method is proposed which comprises addition of a secondary amine compound to a reaction system containing hydrogen peroxide together with a rhenium catalyst (Tetrahedron Letters, Vol. 37, No. 33, pp. 6025–6028, 1996). However, this method has a problem in that a desired N,N-dialkylhydroxylamine compound can hardly be obtained.

An object of the present invention is to provide a method for preparing N,N-disubstituted hydroxylamine compounds. More specifically, the object is to provide a method that enables the preparation of the desired compounds in a high yield by applying a safe and simple reaction step. Another object of the present invention is to provide a method for preparing N,N-disubstituted hydroxylamine compounds which enables, in addition to the aforementioned characteristic features, isolation and purification of the desired compounds without using any special purification apparatuses.

SUMMARY OF THE INVENTION

The inventors of the present invention conducted various studies to achieve the foregoing objects. As a result, they found that N,N-disubstituted hydroxylamine compounds can be safely prepared by an extremely simple reaction step which includes addition of aqueous hydrogen peroxide and a rhenium catalyst to a mixture containing a secondary amine compound and a dehydrating agent. They also found that N,N-disubstituted hydroxylamine compounds can be obtained in a high yield according to this method, because desired products can be readily isolated and purified. The present invention was achieved on the basis of these findings.

The present invention thus provides a method for preparing N,N-disubstituted hydroxylamine compounds represented by formula (II): HO—N($R^1$)($R^2$) wherein $R^1$ and $R^2$ may be the same or different, and independently represent a substituted or unsubstituted alkyl group, a substituted or unsubstituted aryl group, or a substituted or unsubstituted aromatic heterocyclic group, which comprises the step of adding a rhenium catalyst and aqueous hydrogen peroxide to a mixture containing a secondary amine compound represented by formula (I): HN($R^1$)($R^2$) wherein $R^1$ and $R^2$ have the same meanings as those defined above and a dehydrating agent,.

As preferred embodiments of the present invention, there are provided the aforementioned method wherein the rhenium catalyst is methyltrioxorhenium, and the catalyst is used in an amount of 1 molar % or less based on the secondary amine compound represented by the formula (I); the aforementioned method wherein the dehydrating agent is anhydrous magnesium sulfate; the aforementioned method wherein aqueous hydrogen peroxide having a concentration of 60% by weight or less is used; the aforementioned method which comprises the step of dropwise addition of an aqueous hydrogen peroxide that contains a rhenium catalyst dissolved therein; the aforementioned method which comprises the steps of removing the dehydrating agent, and then adding a protonic acid to the reaction system to isolate a protonic acid salt of the N,N-disubstituted hydroxylamine compound represented by formula (III): HO—$N^+$H($R^1$)($R^2$)·X– wherein $R^1$ and $R^2$ have the same meanings as those defined above and X– represents a conjugate base of the protonic acid; the aforementioned method wherein the protonic acid is oxalic acid or maleic acid; and the aforementioned method wherein toluene or ethyl acetate is used as a reaction solvent.

BEST MODE FOR CARRYING OUT THE INVENTION

In the above formulas (I), (II) and (III), $R^1$ and $R^2$ may be the same or different, and represent a substituted or unsubstituted alkyl group, a substituted or unsubstituted aryl group, or a substituted or unsubstituted aromatic heterocyclic group. As to the unsubstituted groups, linear- or branched-chain alkyl groups having 1 to 30 carbon atoms, aryl groups having 6 to 36 carbon atoms, aromatic heterocyclic group having 1 to 10 carbon atoms and the like may preferably be used. $R^1$ and $R^2$ may bind to each other to form a ring.

Examples of the unsubstituted groups independently represented by $R^1$ and $R^2$ include, for example, alkyl groups such as methyl group, ethyl group, propyl group, isopropyl group, butyl group, isobutyl group, pentyl group, hexyl group, octyl group, decyl group, dodecyl group, hexadecyl group, octadecyl group, cyclopropyl group, cyclopentyl group, and cyclohexyl group; aryl groups such as phenyl group, 1-naphthyl group, and 2-naphthyl group; and aromatic heterocyclic group such as 4-pyridyl group, 2-benzothiazolyl group, 1-imidazolyl group, and 1-pyrazolyl group. Among them, methyl group, ethyl group, and propyl group are preferred.

The alkyl groups, the aryl groups, and the aromatic heterocyclic groups represented by $R^1$ and $R^2$ may have one or more substituents. Where they have two or more substituents, the substituents may be the same or different. Examples of the preferably used substituents include, for example, halogen atoms such as fluorine, chlorine, and bromine; alkyl groups, preferably those having 1 to 30 carbon atoms, such as methyl group, ethyl group, propyl group, isopropyl group, butyl group, isobutyl group, pentyl group, hexyl group, octyl group, decyl group, dodecyl group, hexadecyl group, octadecyl group, cyclopropyl group, cyclopentyl group and cyclohexyl group; aryl groups, preferably those having 6 to 20 carbon atoms, such as phenyl group, 1-naphthyl group, and 2-naphthyl group; aromatic heterocyclic groups, preferably those having 1 to 10 carbon atoms, such as 4-pyridyl group, 2-benzothiazolyl group, 1-imidazolyl group, and 1-pyrazolyl group.

Examples of preferably used substituents further include, for example, alkoxy groups, preferably those having 1 to 10 carbon atoms, such as methoxy group, ethoxy group, isopropoxy group, 1-butoxy group, and 1-hexyloxy group; cycloalkyloxy groups, preferably those having 3 to 8 carbon atoms, such as cyclopentyloxy group, and cyclohexyloxy group; aryloxy groups, preferably those having 6 to 20 carbon atoms, such as phenoxy group, 4-methoxyphenoxy group, 4-nitrophenoxy group, and 1-naphthoxy group; heterocyclyloxy group, preferably those having 1 to 10 carbon atoms, such as 2-furyloxy group; alkoxycarbonyl groups, preferably those having 1 to 10 carbon atoms, such as methoxycarbonyl group, ethoxycarbonyl group, and butoxycarbonyl group; aryloxycarbonyl groups, preferably those having 6 to 20 carbon atoms, such as phenoxycarbonyl group, and 2-chlorophenoxycarbonyl group; cyano group; and nitro group.

In formula (III), X– represents a conjugate base of a protonic acid. Preferred examples include, for example, $Cl^-$, $Br^-$, $I^-$, $HSO_4^-$, $HCO_3^-$, $CH_3SO_3^-$, $C_6H_5SO_3^-$, p-$CH_3C_6H_4SO_3^-$, $CH_3COO^-$, $ClCH_2COO^-$, $Cl_3COO^-$, $CF_3COO^-$, $HOOCCOO^-$, $HOOCCH_2CH_2COO^-$, $HOOCCH=CHCOO^-$, $C_6H_5COO^-$, and o-$COOHC_6H_4COO^-$. Among them, $Cl^-$, $Br^-$, $HOOCCOO^-$, $HOOCCH=CHCOO^-$, and $CH_3SO_3^-$ are preferred, and $HOOCCOO^-$ and $HOOCCH=CHCOO^-$ are most preferred.

Specific examples of the N,N-disubstituted hydroxylamine compounds represented by formula (II) are shown below. However, the method of the present invention is not limited to methods for preparing these hydroxylamine compounds.

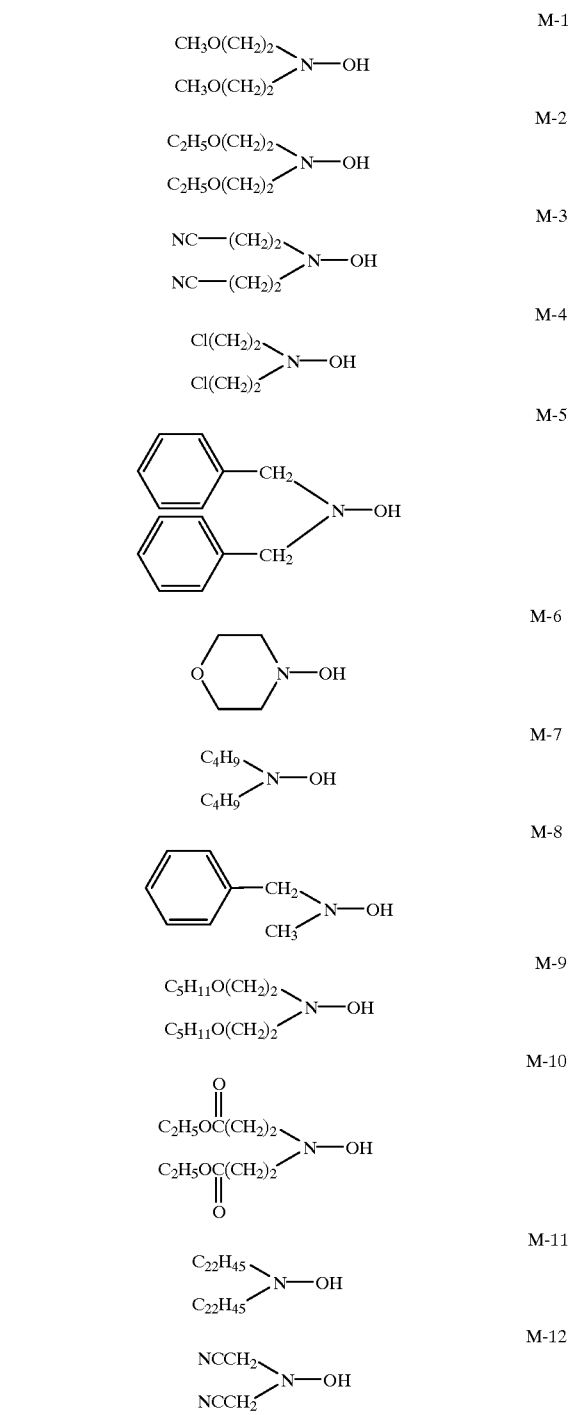

Specific examples of the protonic acid salts of N,N-disubstituted hydroxylamine compounds represented by formula (III) are shown below. However, the method of the present invention is not limited to methods for preparing these protonic acid salts.

-continued

N-10 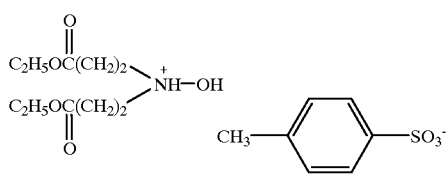

N-11 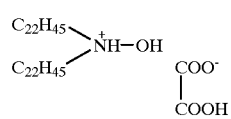

N-12 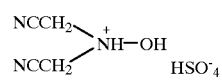

N-13 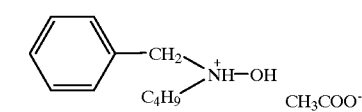

N-14 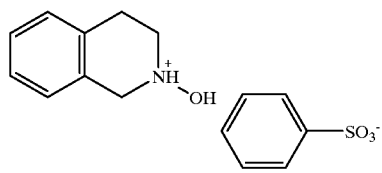

N-15 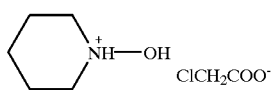

N-16 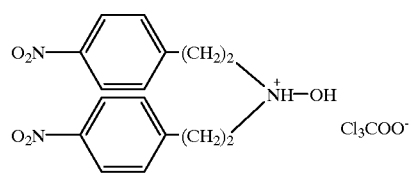

N-17 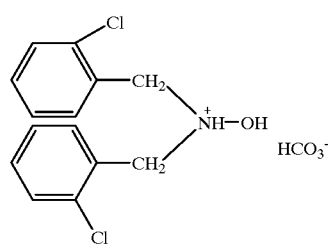

N-18 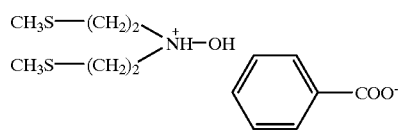

N-19 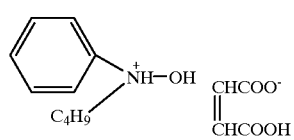

-continued

N-20 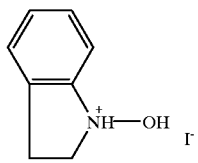

N-21 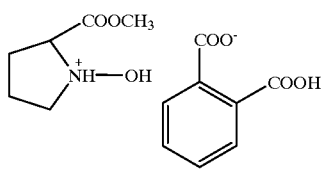

N-22 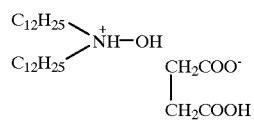

N-23 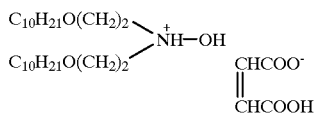

N-24 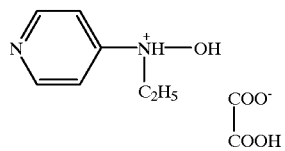

For the preparation of the N,N-disubstituted hydroxylamine compounds represented by the aforementioned formula (II), the method of the present invention is characterized to comprise the step of adding a rhenium catalyst and aqueous hydrogen peroxide to a mixture containing a secondary amine compound represented by the above formula (I) and a dehydrating compound. The secondary amine compounds represented by formula (I), used as a starting material for the method of the present invention, can be readily synthesized according to a known method for preparing an ordinary secondary amine (Shin Jikken Kagaku Koza, Vol. 14, p. 1342, 1978, Maruzen).

According to the method of the present invention, a mixture containing a secondary amine compound represented by formula (I) and a dehydrating agent is preferably prepared in an organic solvent. A type of an organic solvent is not particularly limited so long as the solvent can dissolve the secondary amine compound represented by formula (I) and is inert in the above reaction. One or more organic solvents such as, for example, acetic acid esters such as ethyl acetate and methyl acetate; aromatic hydrocarbons such as benzene, toluene, xylene, and chlorobenzene; lower alcohols such as methanol, ethanol, and isopropanol; chlorine-containing solvents such as methylene chloride and chloroform; ethers such as tetrahydrofuran, dioxane, and 1,3-dioxolane; nitriles such as acetonitrile; and ketones such as acetone and ethyl methyl ketone may be used. The exemplified organic solvents may be used alone or in combination. Preferred solvents include, for example, ethyl acetate, methyl acetate, benzene, toluene, chlorobenzene, and tetrahydrofuran, and most preferred solvents include ethyl acetate and toluene.

A types of a dehydrating agent is not particularly limited. For example, one or more dehydrating agents such as anhydrous magnesium sulfate, anhydrous sodium sulfate, calcium chloride, molecular sieves may be used. Preferably, anhydrous magnesium sulfate and anhydrous sodium sulfate may be used, and anhydrous magnesium sulfate may most preferably be used. An amount of the dehydrating agent is not particularly limited so long as the amount is sufficient to absorb water contained in aqueous hydrogen peroxide, and the amount may be appropriately chosen depending on a type of the dehydrating agent used, water content of the aqueous hydrogen peroxide and other.

A method for adding a rhenium catalyst and aqueous hydrogen peroxide to a mixture containing a secondary amine compound represented by formula (I) and a dehydrating agent, preferably prepared in an organic solvent, is not particularly limited. Examples of preferred applicable methods include, for example, a method of dropwise addition of a solution containing a rhenium catalyst dissolved in aqueous hydrogen peroxide, a method of simultaneous and separate additions of aqueous hydrogen peroxide and a rhenium catalyst, or a method comprising the steps of addition of aqueous hydrogen peroxide and then successive addition of a rhenium catalyst. Preferred examples of applicable methods include a method of dropwise addition of a solution containing a rhenium catalyst dissolved in aqueous hydrogen peroxide, or a method of simultaneous and separate additions of aqueous hydrogen peroxide and a rhenium catalyst. Furthermore, in order to complete the reaction, a method of dropwise addition of an additional solution containing a rhenium catalyst dissolved in a reaction solvent is also effective.

According to the method of the present invention, the molar ratio of aqueous hydrogen peroxide to the secondary amine compound represented by formula (I) may be in the range of from 0.5 to 1.5, preferably from 0.8 to 1.5, and most preferably from 1.0 to 1.3. The rhenium catalyst used for the method of the present invention is not particularly limited. Examples of the rhenium catalyst include, for example, dirhenium heptaoxide, methyltrioxorhenium, tetrabutylammonium perrhenate, dirhenium decacarbonyl, oxotrichlorobistriphenylphosphine rhenium, bromopentacarbonylrhenium, tetramethylrhenium, pentacarbonylhydrorhenium, trioxo($\eta^5$-pentamethylcyclopentadienyl)rhenium, trioxo($\eta^5$-cyclopentadienyl)rhenium, $(CF_3CO_2)ReO_3(THF)_2$, and $(Cl_2CHCO_2)ReO_3(THF)_2$. Among them, preferred examples include trioxo ($\eta^5$-pentamethylcyclopentadienyl) rhenium, tetrabutylammonium perrhenate, oxotrichlorobistriphenylphosphine rhenium, dirhenium heptaoxide, and methyltrioxorhenium, and a most preferred example includes methyltrioxorhenium. These rhenium catalysts may be used in combination.

An applicable amount of the rhenium catalyst is not particularly limited. For example, the amount may be from 0.01 to 5 molar %, preferably from 0.03 to 3 molar %, and most preferably from 0.05 to 1 molar % based on the secondary amine compound represented by formula (I). A suitable amount is desirably chosen depending on a type of the compound represented by formula (I). Methyltrioxorhenium can be synthesized by, for example, the methods described in Journal of Organic Chemistry, 372, 351–370 (1989) and Inorganic Chemistry, 18, 2318 (1979). This catalyst is also available from Aldrich Chemical Co., Inc., U.S.A. as a reagent.

Reaction temperature may be chosen depending on reaction conditions such as a type and an amount of the compound represented by formula (I) and the rhenium catalyst, amount of hydrogen peroxide, and a type of a solvent. Preferably, reaction temperature may be in the range of from −10 to 40° C., and more preferably in the range of from −5 to 30° C. Period of time that is required for the addition of aqueous hydrogen peroxide and the rhenium catalyst is not particularly limited. Preferable period of time for the addition may be from 10 minutes to 5 hours, and more preferably from 10 minutes to 3 hours, which may be suitably chosen depending on reaction conditions mentioned above. It is not preferred to add the whole amount of aqueous hydrogen peroxide at one time, because it may increase risk of explosion. Reaction time after the addition of aqueous hydrogen peroxide and the rhenium catalyst is also not particularly limited. Reaction time may preferably be from 3 minutes to 15 hours, and more preferably from 10 minutes to 10 hours. Reaction time of the whole preparation process is preferably from 5 minutes to 15 hours, and more preferably from 10 minutes to 3 hours. It can be readily understood that these times may be suitably chosen by those skilled in the art depending on the reaction conditions mentioned above.

The N,N-disubstituted hydroxylamine compounds represented by formula (II) can be easily isolated by using conventional means for isolation and purification such as concentration, recrystallization, extraction and, if necessary, distillation, after removal of a dehydrating agent from a reaction mixture. However, without isolation of the N,N-disubstituted hydroxylamine compounds represented by formula (II), a protonic acid salt of the N,N-disubstituted hydroxylamine compounds represented by formula (III) may preferably be formed by adding a protonic acid to a reaction mixture after removal of a dehydrating agent and then isolated. A reaction solvent used for the salt formation may be the same solvent used for the preparation of the compound represented by formula (II). Alternatively, another solvent, in which the resulting protonic acid salt is slightly soluble, may appropriately be used so that crystals of the protonic acid salt can easily be precipitated.

A type of the protonic acid is not particularly limited, and examples include an inorganic acid such as hydrogen chloride, hydrogen bromide, hydrogen iodide, sulfuric acid, and carbonic acid; an organic carboxylic acid such as acetic acid, chloroacetic acid, trichloroacetic acid, trifluoroacetic acid, oxalic acid, succinic acid, maleic acid, benzoic acid, and phthalic acid, or an organic sulfonic acid such as methanesulfonic acid, ethanesulfonic acid, benzenesulfonic acid, and p-toluenesulfonic acid. Among them, hydrogen chloride, oxalic acid, maleic acid, methanesulfonic acid, and p-toluenesulfonic acid are preferred, and oxalic acid and maleic acid are most preferred.

A molar ratio of an applicable amount of the above protonic acid based on the secondary amine compound represented by the formula (I) may be preferably in the range of from 0.7 to 1.3, and more preferably in the range of from 0.8 to 1.1. Reaction temperature for the formation of the protonic acid salt may be preferably from −10 to 40° C., and more preferably from −5 to 30° C. The temperature may be suitably chosen depending on a type of the secondary amine compound represented by formula (I), a type of a solvent and other. Reaction time may also be appropriately chosen, and the reaction time may be preferably from 5 minutes to 5 hours, and more preferably from 10 minutes to 3 hours.

The method of the present invention is characterized in that it comprises a simple and safe reaction step and can produce the desired compound in a higher yield compared to conventional methods. Furthermore, by applying direct isolation of a protonic acid salt of the desired compound from a reaction mixture, the method enables easy isolation of highly purified desired product without using any special purification apparatuses. From a viewpoint of reaction safety, the method of the present invention, where aqueous hydrogen peroxide and the rhenium catalyst are added to a system containing both of the secondary amine compound and the dehydrating agent, can obviate risk of explosion. On the other hand, conventional methods where hydrogen peroxide and the secondary amine compound are allowed to coexist in the same system involve risk of explosion. In addition, water that inhibits the oxidation can be removed by the dehydrating agent, and accordingly, the method of the present invention is advantageous because it eliminates the use of highly concentrated hydrogen peroxide whose handling is possibly dangerous.

EXAMPLES

The present invention will be explained more specifically by referring to the following examples. However, the scope of the present invention is not limited to the examples.

Example 1

Synthesis of Exemplary Compound N-1

Bis(2-methoxyethyl)amine (15 g, 0.113 mole) was added with ethyl acetate (75 ml), and further added with anhydrous magnesium sulfate (15 g), and then the mixture was stirred under ice cooling. A solution of methyltrioxorhenium (0.281 g, 1.126 mmole) dissolved in 35% aqueous hydrogen peroxide (12.8 g, 0.13 mole) was added dropwise to the above mixture over one hour so as to keep internal temperature at from 0° C. to 10° C. After the mixture was stirred at the same temperature for 20 minutes, products in the reaction mixture were quantitatively analyzed by gas chromatography. As a result, it was found that 83% of N,N-bis(2-methoxyethyl)-hydroxylamine (Exemplary Compound M-1), 2% of bis(2-methoxyethyl)amine as the starting material, and 15% of a nitrone compound produced by a further oxidation of the N,N-bis(2-methoxyethyl)hydroxylamine were obtained (the ratios were determined based on ratios of peak area intensity).

After magnesium sulfate was removed by filtration, the filtrate was added with a solution of oxalic acid (9.1 g, 0.101 mole) dissolved in acetone (30 ml). The mixture was stirred for 30 minutes under ice cooling, and the precipitated crystals were collected by filtration to obtain oxalic acid salt of N,N-bis(2-methoxyethyl)-hydroxylamine (19.9 g, yield: 74.0%) having melting point of 81–83° C. Chemical structure of the product was analyzed by $^1$H-NMR, mass spectrometry and elemental analysis. $^1$H-NMR (DMSO-D$_6$) σ (ppm) (multiplicity, integrated value): 10.6–9.10 (br, 3H), 3.51 (t, 4H), 3.26 (s, 6H), 2.90 (t, 4H). Elemental analysis, calculated for $C_8H_{17}N_1O_7$: C, 40.17; H, 7.16; N, 5.86, found: C, 40.12; H, 7.06; N, 6.01.

Example 2

Synthesis of Exemplary Compound N-3

Bis(2-cyanoethyl)amine (3.0 g, 0.0224 mole) was added with ethyl acetate (15 ml) and anhydrous magnesium sulfate (3 g), and the mixture was stirred at room temperature. A solution of methyltrioxorhenium (0.0183 g, 0.0734 mmole) dissolved in 35% aqueous hydrogen peroxide (2.9 g, 0.029 mole) was added dropwise to the mixture while internal temperature was kept at from 20° C. to 30° C. After the reaction mixture was stirred at room temperature for 1 hour, the magnesium sulfate was removed by filtration, and the filtrate was added with a solution of oxalic acid (2.2 g, 0.224 mole) dissolved in acetone (8 ml). The mixture was stirred for 30 minutes under ice cooling, and the precipitated crystals were collected by filtration to obtain oxalic acid salt of N,N-bis(2-cyanoethyl)hydroxylamine (4.2 g, yield: 75.0%) having melting point of 129–130° C. Chemical structure of the product was analyzed by $^1$H-NMR, mass spectrometry and elemental analysis. $^1$H-NMR (DMSO-D$_6$) σ (ppm) (multiplicity, integrated value): 12.0–9.50 (br, 2H), 2.77 (t, 4H), 2.58 (t, 4H). Elemental analysis, calculated for $C_8H_{11}N_3O_5$: C, 41.92; H, 4.84; N, 18.33, found: C, 42.50; H, 4.74; N, 18.38.

Example 3

Synthesis of Exemplary Compound N-4

Bis(2-chloroethyl)amine (3.0 g, 0.0211 mole) was added with ethyl acetate (15 ml) and anhydrous magnesium sulfate (3 g), and the mixture was stirred under ice cooling. A solution of methyltrioxorhenium (0.0104 g, 0.0417 mmole) dissolved in 35% aqueous hydrogen peroxide (2.5 g, 0.025 mole) was added dropwise to the mixture over 1 hour so as to keep internal temperature at from 5° C. to 10° C. After the reaction mixture was stirred at room temperature for 1 hour, the magnesium sulfate was removed by filtration, and the filtrate was added with a solution of oxalic acid (1.9 g, 0.0211 mole) dissolved in acetone (7 ml). The mixture was stirred for 30 minutes under ice cooling, and the precipitated crystals were collected by filtration to obtain oxalic acid salt of N,N-bis(2-chloroethyl)hydroxylamine (3.6 g, yield: 68.0%) having melting point of 134–135° C. Structure of the product was analyzed by $^1$H-NMR and mass spectrometry. $^1$H-NMR (DMSO-D$_6$) σ (ppm) (multiplicity, integrated value): 8.57–7.80 (br, 1H), 5.95–4.96 (br, 1H), 3.71 (t, 4H), 2.92 (t, 4H).

Example 4

Synthesis of Exemplary Compound N-5

Dibenzylamine (3.0 g, 0.0152 mole) was added with ethyl acetate (15 ml) and anhydrous magnesium sulfate (3 g), and the mixture was stirred under ice cooling. A solution of methyltrioxorhenium (0.0114 g, 0.0457 mmole) dissolved in 35% aqueous hydrogen peroxide (1.8 g, 0.018 mole) was added dropwise to the mixture over 1 hour so as to keep internal temperature at 5° C. to 10° C. After the reaction mixture was stirred at the same temperature for 1 hour, the magnesium sulfate was removed by filtration, and the filtrate was added with a solution of oxalic acid (1.23 g, 0.0137 mole) dissolved in acetone (7 ml). The mixture was stirred for 30 minutes under ice cooling, and the precipitated crystals were collected by filtration to obtain oxalic acid salt of N,N-dibenzylhydroxylamine (3.0 g, yield: 65.2%) having melting point of 152–153° C. Chemical structure of the product was analyzed by $^1$H-NMR, mass spectrometry and elemental analysis. $^1$H-NMR (DMSO-D$_6$) σ (ppm) (multiplicity, integrated value): 7.45–7.12 (m, 11H), 3.85 (s, 4H). Elemental analysis, calculated for $C_{16}H_{17}N_1O_5$: C, 63.36; H, 5.65; N, 4.62, found: C, 63.30; H, 5.65; N, 4.62.

Example 5

Synthesis of Exemplary Compound N-6

Morpholine (5.0 g, 0.0574 mole) was added with ethyl acetate (15 ml) and anhydrous magnesium sulfate (6 g), and the mixture was stirred under ice cooling. 35% Aqueous hydrogen peroxide (6.8 g, 0.069 mole) and methyltrioxorhenium (0.0429 g, 0.172 mmole) were added dropwise to the mixture over 1 hour so as to keep internal temperature at 20° C. to 30° C. After the reaction mixture was stirred at room temperature for 1 hour, the magnesium sulfate was removed by filtration, and the filtrate was added with a solution of oxalic acid (4.9 g, 0.0545 mole) dissolved in acetone (15 ml). The mixture was stirred for 30 minutes at room temperature, and the precipitated crystals were collected by filtration to obtain oxalic acid salt of 4-morpholinohydroxylamine (6.4 g, yield: 57.9%) having melting point of 137–138° C. Chemical structure of the product was analyzed by $^1$H-NMR and mass spectrometry. $^1$H-NMR (DMSO-$D_6$) σ (ppm) (multiplicity, integrated value): 12.05–10.95 (br, 3H), 3.82 (d, 2H), 3.45 (t, 2H), 3.10 (d, 4H), 2.75–2.49 (m, 2H).

Comparative Example 1

Synthesis of Exemplary Compound M-1

Ethyl acetate (75 ml) was added with anhydrous magnesium sulfate (15 g), and the mixture was stirred under ice cooling. 35% aqueous hydrogen peroxide (12.8 g, 0.13 mole) was added dropwise to the mixture while internal temperature was kept at 10° C. or lower. Methyltrioxorhenium (0.281 g, 1.126 mmole) was further added to the mixture at the same temperature. Bis(2-methoxyethyl)amine (15 g, 0.113 mole) was added dropwise to the resulting mixture over 1 hour while the internal temperature was kept at 0° C. to 10° C. After the reaction mixture was stirred for 20 minutes at the same temperature, products in the reaction mixture were quantitatively analyzed by gas chromatography. As a result, it was found that 5.6% of N,N-bis(2-methoxyethyl)hydroxylamine, 52.1% of bis(2-methoxyethyl)amine as the starting material, and 40.0% of nitrone compound produced by a further oxidation of the N,N-bis(2-methoxyethyl)hydroxylamine were obtained (the ratios were determined based on ratios of peak area intensity). The results revealed that the desired N,N-disubstituted hydroxylamine compound was hardly obtainable by the method where the secondary amine compound was added to a system in which aqueous hydrogen peroxide and the rhenium catalyst were allowed to coexist.

From the foregoing explanations, it can be readily understood that N,N-disubstituted hydroxylamine compounds and protonic acid salts thereof, which are useful as developing agents of silver halide photosensitive materials, can be efficiently prepared according to the method of the present invention.

What is claimed is:

1. A method for preparing an N,N-disubstituted hydroxylamine compound represented by formula (II): HO—N($R^1$)($R^2$) wherein $R^1$ and $R^2$ may be the same or different, and independently represent a substituted or unsubstituted alkyl group, a substituted or unsubstituted aryl group, or a substituted or unsubstituted aromatic heterocyclic group, which comprises the step of adding a rhenium catalyst and aqueous hydrogen peroxide to a mixture containing a secondary amine compound represented by formula (I): HN($R^1$)($R^2$) wherein $R^1$ and $R^2$ have the same meanings as those defined above and a dehydrating agent.

2. The method according to claim 1, wherein the rhenium catalyst and aqueous hydrogen peroxide is added to said mixture prepared in an organic solvent.

3. The method according to claim 2, wherein toluene or ethyl acetate is used as a reaction solvent.

4. The method according to claim 1, which further comprises the step of adding a protonic acid to the reaction system after removal of the dehydrating agent to isolate a protonic acid salt of the N,N-disubstituted hydroxylamine compound represented by formula (III): HO—$N^+$H($R^1$)($R^2$) ·$X^-$ wherein $R^1$ and $R^2$ have the same meanings as those defined above and $X^-$ represents a conjugate base of the protonic acid.

5. The method according to claim 4, wherein the protonic acid is oxalic acid or maleic acid.

6. The method according to claim 1, wherein aqueous hydrogen peroxide containing the rhenium catalyst dissolved therein is added dropwise to said mixture.

7. The method according to claim 6, wherein the rhenium catalyst is methyltrioxorhenium.

8. The method according to claim 7, wherein the catalyst is used in an amount of 1 molar % or less based on the secondary amine compound represented by the formula (I).

9. The method according to claim 8, wherein the dehydrating agent is anhydrous magnesium sulfate.

10. The method according to claim 9, wherein aqueous hydrogen peroxide having a concentration of 60% by weight or less is used.

11. A method for preparing an N,N-disubstituted hydroxylamine compound represented by formula (II): HO—N($R^1$)($R^2$) wherein $R^1$ and $R^2$ may be the same or different, and independently represent a substituted or unsubstituted alkyl group, a substituted or unsubstituted aryl group, or a substituted or unsubstituted aromatic heterocyclic group, which comprises the steps of:

(a) preparing a mixture containing a secondary amine compound represented by the formula (I): HN($R^1$)($R^2$) wherein $R^1$ and $R^2$ have the same meanings as those defined above and a dehydrating agent in an organic solvent, and (b) adding a rhenium catalyst and aqueous hydrogen peroxide to the mixture.

12. The method according to claim 11, which further comprises the step of:

(c) adding a protonic acid to reaction system after removal of the dehydrating agent to isolate a protonic acid salt of the N,N-disubstituted hydroxylamine compound represented by the formula (III): HO—$N^+$H($R^1$)($R^2$) ·$X^-$ wherein $R^1$ and $R^2$ have the same meanings as those defined above and $X^-$ represents a conjugate base of the protonic acid.

13. The method according to claim 12, wherein aqueous hydrogen peroxide containing the rhenium catalyst dissolved therein is added dropwise to said mixture.

14. The method according to claim 13, wherein the rhenium catalyst is methyltrioxorhenium.

15. The method according to claim 14, wherein the catalyst is used in an amount of 1 molar % or less based on the secondary amine compound represented by the formula (I).

16. The method according to claim 15, wherein the dehydrating agent is anhydrous magnesium sulfate.

17. The method according to claim 16, wherein aqueous hydrogen peroxide having a concentration of 60% by weight or less is used.

18. The method according to claim 17, wherein the protonic acid is oxalic acid or maleic acid.

19. The method according to claim 18, wherein toluene or ethyl acetate is used as a reaction solvent.

* * * * *